United States Patent [19]

Itoh et al.

[11] Patent Number: 4,795,805

[45] Date of Patent: Jan. 3, 1989

[54] DERIVATIVE OF ADULT T CELL LEUKEMIA VIRUS ANTIGEN PEPTIDE

[75] Inventors: Seiga Itoh, Sagamihara; Susumu Sekine, Machida; Tadatsugu Taniguchi, Ibaraki; Mitsuaki Yoshida; Haruo Sugano, both of Tokyo, all of Japan

[73] Assignees: Kyowa Hakko Kogyo Co., Ltd.; Juridical Foundation, Japanese Foundation for Cancer Research, both of Tokyo, Japan

[21] Appl. No.: 104,578

[22] Filed: Oct. 2, 1987

Related U.S. Application Data

[63] Continuation of Ser. No. 696,586, Jan. 31, 1985, abandoned.

[30] Foreign Application Priority Data

Feb. 10, 1984 [JP] Japan .................. 59-24187

[51] Int. Cl.$^4$ .................... C07K 13/00; C12D 21/02
[52] U.S. Cl. .................... 530/350; 530/806; 530/808; 530/820; 530/825; 435/68; 435/70; 935/47; 935/65; 424/89
[58] Field of Search ............... 530/350, 806, 808, 820, 530/825; 435/68, 70; 424/89; 935/47, 65

[56] References Cited

U.S. PATENT DOCUMENTS

| | | | |
|---|---|---|---|
| 4,520,113 | 5/1985 | Gallo | 424/89 |
| 4,572,800 | 2/1986 | Shimizu et al. | 424/88 |
| 4,701,416 | 10/1987 | Nunbery | 435/68 |
| 4,738,922 | 4/1988 | Haseltine et al. | 435/68 |
| 4,745,055 | 5/1988 | Schenk et al. | 435/68 |

FOREIGN PATENT DOCUMENTS 0151475  8/1985  European Pat. Off.

OTHER PUBLICATIONS

Nishi, *DNA*, vol. 2, No. 4 (1983) 265–273.
Nielsen, *P.N.A.S.*, 80, Sep. 1983:5198–5202.
Seiki, *P.N.A.S.*, 80, Jun. 1983:3618–3622.
Casadahm et al, *J. Bacteriology*, vol. 143(2) 1980, pp. 971–980.
Yoshida et al., *PNAS*, 79, 1982, pp. 2031–2035.
Manzari et al. *PNAS*, 80, 1983, pp. 1574–1578.
Oroszlon et al. *PNAS* 79, 1982, pp. 1291–1294.
Hinumn et al. *PNAS* 78(10) 1981, pp. 6476–6480.
Sagata et al., "Identification of a Potential Protease . . . Viruses", *FEBS*, 178(1) 1984, pp. 79–82.
Hamura et al., "Expression of the Gay Gene of HTLV . . . Use," *Gene*, 38, 1985, pp. 57–64.
Geraini et al., "Use of Gene Fusions and Protein . . . Plasmid R6IL", *PNAS*, 80, 1983, pp. 6848–6852.
Weinstach et al., "Open Reading Frame Expression Vectors", *PNAS*, 80, 1983, pp. 4432–4436.

*Primary Examiner*—Johnnie R. Brown
*Assistant Examiner*—Garnette D. Draper
*Attorney, Agent, or Firm*—Fitzpatrick, Cella, Harper & Scinto

[57] ABSTRACT

Recombinant plasmids are constructed by inserting a DNA fragment coding for a fused protein of an adult T cell leukemia virus antigen peptide and an enzyme into a vector DNA. Microorganisms are transformed with the recombinant plasmid and thereafter cultured to express the fused protein. The fused protein is useful for the detection and diagnosis of adult T cell leukemia.

1 Claim, 1 Drawing Sheet

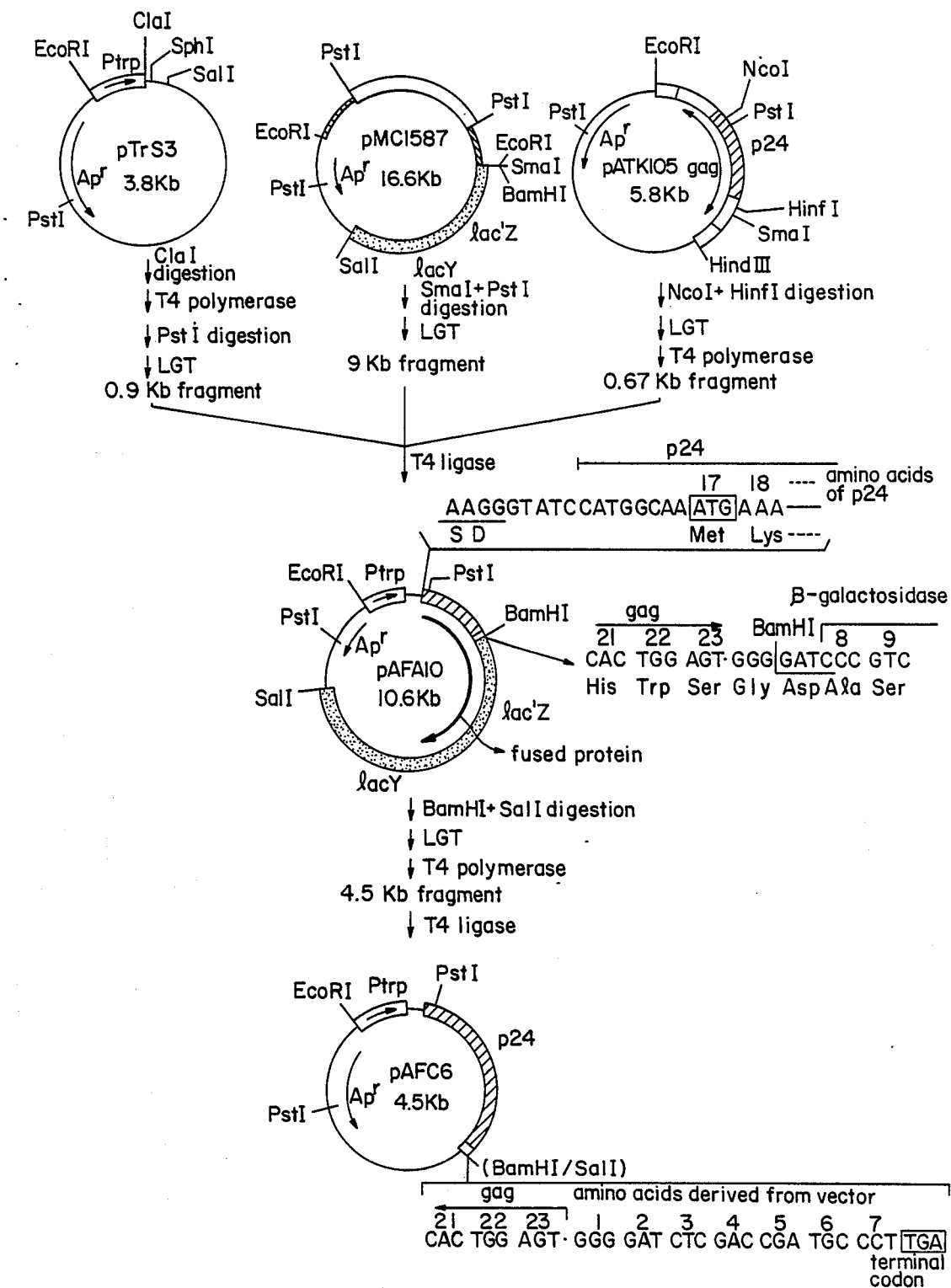

DERIVATIVE OF ADULT T CELL LEUKEMIA VIRUS ANTIGEN PEPTIDE

This application is a continuation of application Ser. No. 696,586 filed Jan. 31, 1985 now abandoned.

BACKGROUND OF THE INVENTION

The present invention relates to a fused protein of an adult T cell leukemia virus antigen peptide and an enzyme, a recombinant plasmid wherein a DNA fragment coding for the peptide and the fused protein is incorporated, a microorganism containing the plasmid and a process for producing the adult T cell leukemia virus antigen peptide or the fused protein of the peptide and the enzyme using the microorganism.

Adult T cell leukemia virus (hereinafter referred to as ATLV), which is a synonym of human T cell leukemia virus (HTLV), is a C-type retrovirus isolated from patients with adult T cell leukemia (hereinafter referred to as ATL) [Yoshida, et al., Proc. Natl. Acad. Sci., USA, 79, 2031–2035 (1982)]. There are numerous reports that ATL patients have a poor prognosis and that efficacious treatment does not exist leading to a 50% mortality rate within a half-year.

In recent years, an antibody which reacts specifically with cultured MT-1 cells derived from ATL has been shown to exist in the serum of ATL patients [Hinuma, et al., Proc. Natl. Acad. Sci., USA, 78, 6476–6480 (1980)]. The existence of this antibody has been confirmed subsequently in all ATL patients and the corresponding antigen is called ATL-associated antigen (hereinafter referred to as ATLA). It has been found that the antibody specific for ATLA (hereinafter referred to as Anti-ATLA antibody) exists in 25% of normal, healthy people in areas with a high incidence of ATL. It has also been shown that the distribution of cases possessing the anti-ATLA antibody corresponds to the regions with high ATL incidence (the reference mentioned above). Furthermore, it has been shown that the C-type retrovirus is generated within MT-1 cells, that ATLA is mainly an antigen of this retrovirus and that the anti-ATLA antibody reacts with a structural protein of th virus, particularly the p24 protein. The existence of ATLV genome in MT-1 cells and the peripheral lymphocytes of patients has been established [Yoshida, et al., Proc. Natl. Acad. Sci., USA, 79, 2031–2035 (1982)]. ATLV has also been detected by culturing the lymphocttes of normal people who are positive to the anti-ATLA antibody.

There is a very close correlation between ATL and ATLV, and ATLV is considered to be the causative virus of ATL. Though the route by which infection occurs is still unknown, it is pointed out that coitus transmission and maternal transmission are the most likely routes because of the familial accumulation of the infection.

Further, transfusion of blood is mentioned as an important route. Actually, there has been a report of a clinical example showing that transfusion of blood positive to the anti-ATLA antibody caused the receptor to become positive to the anti-ATLA antibody. As 25% of healthy people in areas with a high incidence of ATL are anti-ATLA antibody positive, the likelihood of their being carriers of ATLV is extremely high, which means that they must be avoided as blood transfusion donors.

The detection of the anti-ATLA antibody is now carried out by the indirect fluorescence antibody method using acetone fixed slides of cultured cells derived from ATL. However, the method is inconvenient for the purpose of analyzing many serum samples rapidly at a time.

In the case of other infectious diseases, it has been known that the detection method using an antigen itself instead of cells is useful. A method using a cell extract of the cultured cells derived from ATL, such as MT-2, as an antigen has been studied. However, the method has the following problems: (1) the culturing of cells is expensive, (2) there is a problem of safety in the mass production of these cells producing ATLV, (3) the amount of the antigen extracted from cells is limited. Therefore, a method for producing ATLA at low cost and in a large amount is still in demand.

The present inventors studied about a method for providing ATLA which is useful for the detection of the anti-ATLA antibody in a large amount and at low cost. As the result, it was found that an ATLV antigen peptide was accumulated in a large amount by culturing a microorganism containing a recombinant DNA which was obtained by incorporating a DNA fragment of gag gene coding for the main antigen peptide p24 in the ATLV genome into a vector DNA by recombinant DNA techniques (Japanese Patent Application No. 170908/83).

The present inventors have further studied for the purpose of more efficient expression. To this end, a recombinant DNA which is useful for the production of a fused protein of an antigen peptide and an enzyme, which is expected to be useful for the simple detection of the antigen peptide and the actual detection of the anti-ATLA antibody, has been prepared and efficient production of said fused protein by a microorganism containing said DNA has now been confirmed.

SUMMARY OF THE INVENTION

The present invention provides a fused protein of an ATLV antigen peptide and an enzyme, a recombinant plasmid wherein a DNA fragment coding for the peptide and the fused protein is incorporated, a microorganism containing the plasmid, and a process for producing the ATLV antigen peptide and the fused protein of the ATLV antigen peptide and the enzyme using the microorganism.

BRIEF DESCRIPTION OF THE DRAWING

FIG. 1 is a flow/sheet for constructing pAFA10 and pAFC6.

DESCRIPTION OF THE INVENTION

The present invention provides a fused protein of an ATLV antigen peptide and an enzyme, a recombinant plasmid wherein a DNA fragment coding for the peptide and the fused protein is incorporated, a microorganism containing the plasmid, and a process for producing the ATLV antigen peptide and the fused protein of the ATLV antigen peptide and the enzyme using the microorganism.

The construction of the recombinant plasmid of the present invention is carried out in the following manner.

The recombinant plasmid wherein a DNA coding for a fused protein of an ATLV antigen peptide and an enzyme is incorporated can be constructed by incorporating a DNA coding for the ATLV antigen peptide and a DNA coding for the enzyme into a vector DNA using recombinant DNA techniques.

As structural proteins of the ATLV particle, p11, p14, p17, p24 and p45 are known. The most commonly appearing protein among these is p24 and it has a high reactivity with the serum of ATL patients. Further, in the cultured cells derived frmm ATL cells such as MT-1 and MT-2, p24 is highly expressed. Thus, it is apparent that p24 is the main ATLV antigen peptide, which is obvious also from the fact that p24 was the first to be purified and studied.

Moreover, it is assumed that since sera positive to the anti-ATLA antibody, almost without exception, allow the immune agglutination of p24, most anti-ATLA antibody patients have at least an antibody against p24. Therefore, the use of p24 as an antigen in the analysis of a wide range of sera is considered to be the most general and appropriate.

In recent years, a method of detecting an antigen using an antibody combined with an enzyme has been developed and frequently applied. The method is a very simple method with a high sensitivity, in which a complex of the enzyme and the antibody and the antigen are detected by adding a substrate corresponding to the enzyme at the latest stage and expressing the decomposed substrate. As the enzymes generally used for the purpose, peroxidase, alkaline phosphatase and $\beta$-galactosidase are mentioned. A fused protein obtained by the fusion of the antigen, i.e. ATLV peptide and such an enzyme is expected to be most effectively used by adding appropriate modification to the antigen detection method described above, since the fused protein has both the antigenic property of the ATLV antigen peptide and the activity of the enzyme. Further, there is not any appropriate method for the quantitative determination and the determination of purity in the process of purification of the produced ATLV antigen peptide. The method using the anti-serum of the patient is the only feasible method but is not desirable because the amount of such anti-serum is limited and there is a problem of safety. However, if it is designed initially to produce a fused protein of the antigen peptide and an appropriate enzyme, determination and detection of the antigen peptide can readily be carried out by measuring the activity of the enzyme.

The present inventors have studied about a process for producing a fused protein of the ATLV antigen peptide and an enzyme, especially $\beta$-galactosidase.

The plasmid pATK03 cloned by Seiki, et al. [Seiki, et al.: Proc. Natl. Acad. Sci., USA, 80, 3618–3622 (1983)] and its derivative pATK105 constructed by the present inventors (Japanese Pat. Application No. 170908/83) can be used as a source of the DNA coding for the ATLV antigen peptide. The ATLV genome consists of the LTR at both ends and at least 3 genes, namely, gag, pol, and env. It is assumed that, p24, which is the virus antigen about which the most detailed research is being conducted, is a product of the gag gene as it is a core protein of the virus. Actually, the DNA sequence coding for the amino acid sequence of p24 determined by Oroszlan, et al. [Oroszlan, et al.: Proc. Natl. Acad. Sci., USA, 79, 1291–1294 (1982)] was detected in the gag gene.

pATK03 is a clone containing 5'LTR, gag and a part of pol, whereas pATK105 contains only the gag part and does not contain the 5'LTR and the part of pol. Therefore, the latter is preferable for the treatment of gag gene DNA.

As the DNA coding for $\beta$-galactosidase, for example, pMC1587 containing Escherichia coli $\beta$-galactosidase gene can be used. pMC1587 is a plasmid which can be recovered from Escherichia coli EMC1587, FERM BP-484 by a conventional method and the restriction map thereof is illustrated in FIG. 1. $\beta$-galactosidase gene of pMC1587 named lac'Z lacks 8 amino acids from the N-terminal and restriction enzyme cleavage sites for EcoRI, SmaI and BamHI are located just before lac'Z. Since the activity of $\beta$-galactosidase does not change even if 22 amino acids are removed from the N-terminal, the enzyme encoded by pMC1587 naturally retains its enzyme activity. A fused gene of the gaq gene and lac'Z can be constructed by using the three restriction enzyme cleavage sites.

Any vector DNA can be utilized, provided that the inserted DNA is expressible within a microorganism. It is preferred to use a plasmid which includes a suitable promoter such as a tryptophan (trp) or lactose (lac) promoter downstream from which the subject DNA can be inserted and which has a suitable distance such as 6–18 base pairs, between the Shine-Dalgarno sequence (hereinafter referred to as SD sequence) and the translation initiation codon (ATG). One of the most suitable plasmids is pTrS3. Plasmid pTrS3 is constructed by the method described in Reference Example. Since pTrS3 has addistance (SD-ATG) of 13 base pairs between the SD sequence and the translation initiation codon (ATG) downstream from the tryptophan promoter and a foreign DNA can be inserted immediately after ATG, any gene which has the frame conforming with the ATG will be expressed directly and efficiently using this vector.

Recombination of a DNA coding for the ATLV antigen peptide such as the DNA coding for p24 from pATK105 and a vector DNA such as pTr33 can be carried out using general recombinant DNA techniques in which both DNAs are digested with restriction enzymes followed by ligation using T4 DNA ligase.

Further, ligation of a DNA coding for the ATLV antigen peptide such as the DNA coding for p24 from pATK105 and a DNA coding for an enzyme such as $\beta$-galactosidase, for example, the lac'Z gene of pMC1587 and recombination of the DNAs into a vector DNA such as pTrS3 can also be carried out using general recombinant DNA techniques in which both DNAs are digested with restriction enzymes followed by ligation using T4 DNA ligase. Ligation may be conducted by a method employing fill-in reaction with DNA polymerase I.Klenow fragment or a method using DNA linker.

In the case of pATK105, pMC1587 and pTrS3 mentioned as examples, as shown in FIG. 1, an NcoI-SmaI fragment containing most part of p24 of pATK105, a SmaI-PstI fragment containing the lac'Z of pMC1587 and a PstI-ClaI fragment containing the tryptophan promoter of pTrS3 are combined to construct recombinant plasmid pAFA10 coding for a fused protein of p24 and $\beta$-galactosidase. Further, recombinant plasmid pAFC6 coding for a large portion of p24 can be constructed by removing the $\beta$-galactosidase gene part from pAFA10 by the cleavage with BamHI and SalI and recombining by fill-in reaction with T4 polymerase.

The reaction conditions necessary for the abovedescribed preparation of the recombinant plasmid are generally as follows. DNA digestion with restriction enzymes is normally carried out by 15 minutes–24 hours digestion of 0.1–100 $\mu$g of DNA, at 18°–42° C., preferably 32°–38° C., using 0.1–300 units, preferably 1–3 units, of restriction enzyme per 1 $\mu$g of DNA in 2–200 mM, preferably 10-40 mMTTris-HCl (pH 6.0-9.5, preferably pH 7.0-8.0), 1-150 mmM NaCl and 2-20 mM, preferably 5-10 mM $MgCl_2$. The reaction is terminated by heating at 55°-75° C., preferably 63°-70° C., for 5-30 minutes. The restriction enzymes may be inactivated by reagents such as phenol and diethyl pyrocarbonate. Synthetic oligonucleotides are prepared by the diethyl phosphate method [H. G. Khorana, et al.: J. Mol. Biol., 72, 20 (1972)], the phosphotriester method [R. Crea, et al.: Proc. Natl. Acad. Sci., USA, 75, 5765 (1978)] or the phosphite method [M. D. Matteucci, et al.: J. Am. Chem. Soc. 103, 3185 (1981)].

Phosphorylation of the synthetic oligonucleotides is conducted at 20°-40° C., preferably 35°-38° C. for 5 minutes to 2 hours, using 0.1-100 units of T4 polynucleotide kinase in 2-200 mM, preferably 10-70 mM Tris-HCl (pH 6.0-9.5, preferably pH 7.0-8.0), 3-20 mM, preferably 4-10 mmM $MgCl_2$ and 1-10 mM dithiothreitol. Ligation of DNA fragments is conducted at 1°-37° C., preferably 3°-20° C., for 15 minutes to 72 hours, preferably 2-20 hours using 0.1-10 units of T4 DNA ligase in 2-200 mM, preferably 10-70 mM Tris-HCl (pH 6.0-9.5, preferably pH 7.0-8.0), 2-20 mM, preferably 5-10 mM $MgCl_2$, 0.1-10 mM, preferably 0.5-2 mM ATP and 1-50 mM, preferably 5-10 mM dithiothreitol.

Purification of the DNA fragments, recombinant plasmids, etc. is carried out by agarose gel electrophoresis.

The ATLV antigen peptide is obtained by culturing a transformant obtained by introducing a recombinant plasmid such as pAFA10 or pAFC6 into a microorganism.

Any microorganism is employable, provided that the recombinant plasmid can be expressed in the microorganism. It is desirable to use *Escherichia coli*, and *Escherichia coli* K-12, HB101 or SG4008 [Gottesman & Zipser, J. Bact., 133, 844-851 (1978)] is preferably used.

Transformation is carried out according to the method of S. N. Cohen, et al. [Proc. Natl. Acad. Sci., USA, 69, 2110 (1972)]. Transformants are obtained as ampicillinresistant strains in the cases of pAFA10 and pAFC6. By culturing *Escherichia coli* carrying pAFA10 or pAFC6 in a medium, a fused protein of the ATLV antigen peptide and β-galactosidase is produced in the culture medium.

The method of producing the ATLV antigen peptide by a micoorganism containing pAFC6 carrying an incorporated DNA fragment which codes for the ATLV antigen peptide and is obtained by removing a DNA fragment coding for β-galactosidase from pAFC10 is more useful than that using a microorganism containing a plasmid carrying an incorporated DNA fragment coding for the ATLV antigen peptide which is not subjected to fusion because a microorganism having a high productivity can be selected by the indication of β-galactosidase activity and thereafter the β-galactosidase part is readily removable from the plasmid.

As the medium, either a synthetic medium or a natural medium can be used so long as it is suitable for the growth of *Escherichia coli* and the production of the fused protein.

As a carbon source, glucose, fructose, lactose, glycerol, mannitol, sorbitol, etc. may be used. As a nitrogen source, $NH_4Cl$, $(NH_4)_2SO_4$, casamino acid, yeast extract, polypeptone, meat extract, Bacto-trypton, corn steep liquor, etc. may be used. In addition, nutrients such as $K_2HPO_4$, $KH_2PO_4$, NaCl, $MgSO_4$, vitamine $B_1$ and $MgCl_2$ may be used.

Culturing is carried out at pH 5.5-8.5 and at 18°-40° C. with aeration and stirring.

After culturing for 5-90 hours, the fused protein of hhe ATLV antigen peptide and *Escherichia coli* β-galactosidase is accumulated in cultured cells. The collected cells are disrupted by ultrasonic disintegration nnd subjected to centrifugation. The polypeptide is recovered from the supernatant fluid according to a conventional method.

Determination of the fused protein of the ATLV antigen peptide and β-galactosidase is carried out by fractionating the protein by SDS polyacrylamide gel electrophoresis [Laemmli, Nature, 227, 680 (1970)], staining the fractionated protein and subjecting the protein to gel scanner. Determination of the fused protein is also carried out by measuring the β-galactosidase activity according to the method of Miller [Miller, Experiments in Molecular Genetics, pp. 352-355, Cold Spring Harbor Laboratory (1972)].

Isolation of the plasmids from the microorganisms is carried out in accordance with the method of H. C. Birnboim, et al.: Nucleic Acids Research 7, 1513 (1979).

Certain specific embodiments of the invention are illustrated by the following representative examples.

EXAMPLE 1

Construction of a recombinant plasmid, pAFA10 which produces a fused protein containing the gag and β-galactosidase (FIG. 1):

A DNA fragment containing the region coding for a large portion of p24 and the part downstream therefrom was cut out from pATK105 and was ligated with β-galactosidase. gene (lac'Z) cut out from pMC1587, and the recombinant DNA was inserted downstream from the trp promoter of expression vector pTrS3 in the following manner.

10 μg of pATK105 [5.8 kilobases (referred to as Kb hereinafter)] which was recovered from *Escherichia coli* EATK105, FERM BP-340 by the method described in Reference Example 1 was dissolved in 100 μl (total volume) of a solution consisting of 10 mM Tris-HCl (pH 7.5), 10 mM $MgCl_2$, 10 mM dithiothreitol and 50 mM NaCl (referred to as Y-50 buffer solution hereinafter). 20 units of NcoI (product of New England Biolabs) and 20 units of HinII (product of Takara Shuzo Co., the restriction enzymes hereinafter are all products of Takara Shuzo Co., unless otherwise specified) were added and digestion reaction was carried out at 37° C. for 3 hours. The reaction solution was heated at 65° C. for 10 minutes to inactivate the enzymes and subjected to the purification by low-gelling-temperature agarose gel electrophoresis (referred to as LGT method hereinafter) to obtain 0.5 μg of a DNA fragment of 0.67 Kb containing a large portion of p24. 0.5 μg of the DNA fragment was dissolved in 30 μl of a solution consisting of 67 mM TrisHCl (pH 8.8), 6.7 mM $MgCl_2$, 10 mM 2-mercaptoethanol, 6.8 μM EDTA, 16.6 mM $(NH_4)_2SO_4$ and 1 mM each dATP, dTTP, dGTP and dCTP (referred to as T4 DNA polymerase buffer solution hereinafter). 5 units of T4 DNA polymerase (product of Takara Shuzo Co.) was added and fill-in reaction was carried out at 37° C. for 1 hour. The reaction solution was heated at 65° C. for 10 minutes to inactivate the enzyme. The DNA fragment contains the DNA- from the 41st base from 5′ terminal to the 66th base downstream from 3′ terminal of p24 in ATLV gag gene.

10 μg of pMC1587 (16.6 Kb) was dissolved in 100 μl of Y-50 buffer solution and 20 units each of SmaI and PstI were added. Digestion reaction was carried out at 37° C. for 3 hours. The reaction solution was heated at 65° C. for 1 minutes to inactivate the enzymes. About 2 μg of a DNA fragment of about 9 Kb containing β-galactosidase gene was obtained by LGT method.

Separately, 10 μg of pTrS3 (3.8 Kb) recovered from Escherichia coli ITrS3, FERM BP-328 by the method of Reference Example 3 was dissolved in 100 μl (total volume) of Y-50 buffer solution. 20 units of ClaI (product of Boehringer Mannheim GmbH) was added and digestion reaction was carried out at 37° C. for 3 hours. The reaction solution was heated at 65° C. for 10 minutes to inactivate the enzyme and a DNA was recovered by ethanol precipitation. The DNA was dissolved in 100 μl of Y-50 buffer solution and 20 units of PstI was added. Digestion reaction was carried out at 37° C. for 3 hours and about 1 μg of a DNA fragment of about 0.9 Kb containing trp promoterwwas obtained by LGT method.

0.1 μg of the resulting DNA fragment, 0.1 μg of the NcoI-HinfI fragment of pATK105 obtained by fill-in reaction as described above and 1 μg of the SmaI-PstI fragment of pMC1587 were dissolved in 50 μl of a solution consisting of 20 mM Tris-HCl (pH 7.1), 10 mM MgCl$_2$, 10 mM dithiothreitol and 1 mM ATP (referred to as T4 ligase buffer solution hereinafter). 2.5 units of T4 DNA ligase (product of Takara Shuzo Co.) was added and ligation reaction was carried out at 4° C. for 16 hours. Escherichia coli K-12, HB101 was transformed with the reaction solution by a conventional eethod to obtain an ampicillin-resistant (Apr) strain. Recombinant plasmid pAFA10 (about 10.6 Kb) was obtained from the strain by a conventional method. The structure of pAFA10 was confirmed by agarose gel electrophoresis after digestion with EcoRI, PstI and BamHI. The polypeptide encoded by pAFA10 was a fused protein with a total of 1249 amino acids wherein the ATLV antigen peptide of 221 amino acids which starts with methionine which is the 17th amino acid from the N-terminal of p24, RAS 23 and amino acids which are the product of gag gene other than p24 at the C-terminal and β-galactosidase which lacks 7 amino acids from N-terminal were fused. (Refer to FIG. 1.)

Escherichia coli K-12, HB101 containing plasmid pAFA10 was deposited with the American Type Culture Collection, U.S.A. as Escherichia coli EAFA10, ATCC39582 on Jan. 19, 1984.

EXAMPLE 2

Removal of β-galactosidase gene from pAFA10:

The β-galactosidase gene part is removed from pAFA10 coding for the fused protein of the ATLV antigen peptide and Escherichia coli β-galactosidase for the production of the ATLV antigen peptide.

10 μg of pAFA10 (about 10.6 Kb) obtained in Example 1 was dissolved in 100 μl (total volume) of a solution consisting of 10 mM Tris-HCl (pH 7.5), 10 mM MgCl$_2$, 10 mM dithiothreitol and 150 mM NaCl. 20 units each of BamHI and SalI were added and digestion reaction was carried out at 337° C. for 3 hours. About 1.5 μg of a DNA fragment of about 4.5 Kb was recovered from the reactions solution by LGT method. 1.5 μg of the DNA fragment was dissolved in 50 μl of T4 DNA polymerase buffer solution. 5 units of T4 DNA polymerase was added and fill-in reaction was carried out at 37° C. for 1 hour. The reattion solution was heated at 65° C. for 10 minutes to inactivate the enzyme and a DNA was recovered by ethanol precipitation.

0.1 μg of the DNA fragment was dissolved in 50 μl of T4 ligase buffer solution. 2.5 units of T4 ligase was added and ligation reaction was carried out at 4° C. for 16 hours. Escherichia coli K-12, HB101 was transformed using the reaction solution by a conventional method to obtain an Apr strain. Recombinant plasmid pAFC6 (about 4.5 Kb) was obtained from the strain by a conventional method. The structure of pAFC6 was confirmed by agarose gel electrophoresis after digestion with EcoRI and PstI., The polypeptide encoded by pAFC6 started with methionine which is the 17th amino acid from the N-terminal of p24 and had 23 amino acids of gag protein other than p24 and 7 amino acids derived rrom pBR322 which were attached to the C-terminal (refer to FIG. 1).

Escherichia coli K-12, HB101 containing plasmid pAFC6 was deposited with the American Type Culture Collection, U.S.A. as Escherichia coli EAFC6, ATCC39581 on Jan. 19, 1984.

EXAMPLE 3

Production of ATLV antigen peptide and a fused protein of the ATLV angigen peptide and β-galactosidase by Escherichia coli carrying pAFC6 and pAFA10: Escherichia coli HB101 strains carrying recombinant plasmids pAFA10 and pAFC6 obtained in Examples 1 and 2 and vector pTrS3 as a control were inoculated in MCG medium (pH 7.2) consisting of 0.6% Na$_2$HPO$_4$, 0.3% KH$_2$PO$_4$, 0.5% NaCl, 0.1% NH$_4$Cl, 0.5% camamino acid, 1 mM MgSO$_4$ and 4 μg/ml vitamine B$_1$ and culturing was carried out at 30° C. for 4 –16 hours. The culture medium was centifuged at 10,000 rpm for 5 minutes and the collected cells were washed with 30 mM NaCl and 30 mM Tris-HCl (pH 7.5). The cells corresponding to about 20 μg of protein were suspended in 10–20 μl of the sample buffer of Laemmli [Laemmli, Nature, 227, 680 (1970)]. The suspension was heated at 100° C. for 5 minutes to lyse cells. The solution was subjected to SDS-polyacrylamide gel electrophoresis by the method of Laemmli (the reference mentioned above) and staining with Coomassie Brilliant Blue to detect the band of proteins.

As the result, the band of a molecular weight of about 141,000 and that of a molecular weight of about 25,000 were respectively detected in pAFA10 and pAFC6, whereas such bands of proteins were not detected in the control pTrS3. The molecular weights indicatd by the bands of pAFA10 and pAFC6 were almost the same as the molecular weights calculated from the DNA sequences of the gene coding for ATLV antigen peptide-β-galactosidase fused protein and the ATLV antige peptide gene respectively contained in these plasmids. TThe produced polypeptides were determined by drying the SDS-polyacrylamide gel used for the detection, subjecting the gel to gel scanner and measuring the amount of each protein from the strength of each band. As the result, it was found that both the protein o a molecular weight of about 141,000 of pAFA10 and that of about 25,000 of pAFC6 eere produced in an amount of about 20% of the whole cell protein.

As for the case of pAFA10, the activity of β-galactosidase was determined by the method of Miller [Miller, Experiments in Molecular Genetics, pp 352–355, Cold Spring Harbor Laboratory (1972)]. As the result, about 20,000 units of the enzyme activity per 1 ml of the medium was detected. Thus, it was confirmed that the fused protein had the activity of β-galactosidase and therefore the protein is extremely useful as the clinical diagnosis reagent and in the process of purification, etc.

REFERENCE EXAMPLE 1

Insertion of the ATLV gag gene fragment into the expression vector pTrS3:

Subcloning of the gag gene of plasmid pATK03: 600 μg of pATK03 was dissolved in 2 ml (total volume) of a solution consisting of 20 mM Tris-HCl (pH 7.5), 10 mM MgCl$_2$, 10 mM dithiothreitol and 100 mM NaCl. Then, 1,000 units of restriction enzyme ApaI (product of Boehringer Mannheim GmbH) was added and digestion was carried out at 37° C. for 6 hours. DNA fragments were isolated by subjecting the digest to agarose gel electrophoresis in the following manner. Hydroxyl apatite (product of Bio Rad Co., hereinafter referred to as HAP) was put into a groove formed directly in front of the desired fragment of 2.7 Kb on the gel. Electrophoresis was continued and when the subject band was readsorbed on the HAP, the DNA fragment-adsorbed HAP was collected with a pasteur pipette and put on a Sephadex G-50 column (1 cm×20 cm) which had been equilibrated with 10 mM Tris-HCl (pH 7.5). DNA fragments were dissociated from the HAP with 0.5M EDTA (pH 8.0) and elution was continued with 10 mM Tris-HCl (pH 7.5) to obtain the DNA fraction. After phenol and chloroform extraction of the fraction, a DNA fragment of 2.7 Kb was recovered by ethanol precipitation. Hereinafter, the method for recovery of a DNA fragment using agarose gel electrophoresis and HAP is referre to as AGE-HAP.

Then, 40 μg of the DNA fragment was dissolved in 100 μl (total volume) of a solution consisting of 20 mM Tris-HCl (pH 7.5), 10 mM MgCl$_2$ and 10 mM dithiothreitol. 10 units of restriction enzyme HaeII was added and partial digestion of the DNA fragment was carried out at 37° C. for 15 minutes. The reaction solution was subjected to AGE-HAP and 5 μg of a DNA fragment of 1,795 base pairs (bp) was obtained. Then, 5 μg of the DNA fragment was dissolved in a solution consisting of 50 mM Tris-HCl (pH 7.8), 5 mM MgCl$_2$ and 1 mM dithiothreitol, and 1 mM each dATP, dTTP, dGTP and dCTP wrre added together with 15 units of *Escherichia coli* DNA polymerase I.Klenow fragment (Bethesda Research Laboratories Inc., hereinafter referred to as BRL). Fill-in reaction was performed at 15° C. for 3 hours.

Separately, 4.8 μg of EcoRI linker (product of Takara Shuzo Co.) was dissolved in 30 μl (total volume) of a solution consisting of 50 mM Tris-HCl (pH 7.5), 10 mM MgCl$_2$, 5 mM dithiothreitol and 1 mM ATP. Five units of T4 polynucleotide kinase (product of Takara Shuzo Co.) was added and the mixture was subjected to phosphorylation reaction. Then, 2.4 μg of phosphorylated EcoRI linker was mixed with 5 μg of the fragment partially digested with HaeII and described above. The mixture was then dissolved in 50 μl (total volume) of a solution consisting of 20 mM Tris-HCl (pH 7.6), 10 mM MgCl$_2$, 10 mM dithiothreitol and 1 mM ATP, followed by addition of 2.5 units of T4 DNA ligase. After ligation at 4° C. for 16 hours, he whole DNA was recovered by ethanol precipitation.

Then, 4 μg of the DNA fragment with attached EcoRI linker was dissolved in 100 μl of a solution consisting of 20 mM Tris-HCl (pH 7.5), 10 mM MgCl$_2$ and 60 mM NaCl. Five units each of EcoRI and HindIII were added and digestion reaction was carried out at 37° C. for 2 hours. From this digest, 1.5 μg of an EcoRI-HindIII digested fragment of 1,453 bp was obtained by AGE-HAP.

Separately, 5 μg of pBR322 (4.4 Kb) [Bolivar, et al.: Gene, 2, 95 (1977)] was dissolved in 100 μl of a solution consisting of 20 mM Tris-HCl, 10 mM MgCl$_2$ and 10 mM dithiothreitol. Then, 5 units each of EcoRI and HindIII were added and digestion was carried out at 37° C. for 2 hours. 2.5 μg of an EcoRI-HindIII fragment of about 4.3 Kb was recovered by AGE-HAP.

0.2 μg of the fragment and 0.35 μg of the EcoRIHindIII fragment of 1,453 base pairs from pATK03 described above were dissolved in 50 μl (total volume) of a solution consisting of 20 mM Tris-HCl (pH 7.6), 10 mM MgCl$_2$, 10 mM dithiothreitol and 1 mM ATP. Then, 2.5 units of T4 DNA ligasewas added and ligation reaction was carried out at 4° C. for 16 hours.

Using this ligation solution, *Escherichia coli* K-12, HB101 [Bolivar, et al.: Gene 2, 75 (1977)] was transformed by conventional technique and an ampicillinresistant (Ap$^R$) strain was obtained. Recombinant plasmid pATK105 was isolated from the strain by conventional technique. The structure of pATK105 was determined by AGE after digestion with EcoRI, HindIII and PstI. *Escherichia coli* K-12, HB101 containing plasmid pATK105 has been deposited with the Fermentation Research Institute, Agency of Industrial Science and Technology (FERM) as *Escherichia coli* EATK105, FERM BP-340.

REFERENCE EXAMPLE 2

Construction of pKYP100:

50 μg of pKYP10 prepared by the method described in Japanese Published Unexamined Patent Application No. 110600/83 was digested with 50 units of HhaI in 100 μl (total volume) of a reaction solution consisting of 10 mM Tris-HCl (pH 7.5), 7 mM MgCl$_2$ and 6 mM 2-mercaptoethanol at 37° C. for 2 hours. After digestion with HhaI, a DNA fragment of about 180 bp containing the trp promoter was purified by 5% polyacrylamide gel electrophoresis [A. M. Maxam, et al.: Proc. Natl. Acad. Sci. 74, 560 (1977), referred to as PAGE hereinafter]. In the purification step, two DNA fragments other than the desired DNA were obtained because of incomplete purification by PAGE. The three purified DNA fragments (total amount: about 4 μg) were allowed to react with 8 units of *Escherichia coli* DNA polymerase I.Klenow fragment in 30 μl (total volume) of a reaction solution consisting of 50 mM Tris-HCl (pH 7.6), 7 mM MgCl$_2$, 10 mM 2-mercaptoethanol, 0.25 mM dATP, 0.25 mM dCPT, 0.25 mM dGTP and 0.25 mM dTTP at 15° C. for 2 hours. By the reaction, the 3'-protruding end formed by the HhaI digestion was changed to a flush nnd by the 3'→5' exonuclease activity and 5'→3' repairing synthesis activity of DNA polymerase I.Klenow fragment. Subsequently, DNA polymerase I.Klenow fragment was inactivated by heating at 72° C. for 30 minutes and the NaCl concentration was adjusted to 50 mM with 1M NaCl. 8 units of HindIII was added and the mixture was allowed to react at 37° C. for 2 hours. After the digestion with HindIII, a DNA fragment of about 100 bp containing the trp promoter was isolated and purified by PAGE.

Separately, 5 μg of plasmid pBR322 was digested with 8 units of EcoRI in 20 μl (total volume) of a reaction solution consisting of 10 mM Tris-HCl (pH 7.5), 50 mM NaCl, 7 mM MgCl$_2$ and 6 mM 2-mercaptoethanol at 37° C. for 2 hours. After phenol and chloroform extraction and ethanol precipitation, the precipitated DNA fragment was dissolved in 20 µl (total volume) of a mixture of 50 mM Tris-HCl (pH 7.6), 7 mM MgCl$_2$, 6 mM 2-mercaptoethanol, 0.25 mM dATP, 0.25 mM dCTP, 0.25 mM dGTP and 0.25 mM dTTP. Then, 8 units of Escherichia coli DNA polymerase I.Klenow fragment was added and the mixture was allowed to react at 15° C. for 2 hours. The 5'-protruding end formed by the EcoRI digestion was changed to a flush end by the repairing synthesis activity of DNA polymerase I.Klenow fragment. The DNA polymerase I.-Klenow fragment was inactivated by heating at 72° C. for 30 minutes and the NaCl cnncentration was adjusted to 50 mM with 1M NaCl. 8 units of HindIII was added and the mixture was allowed to react at 37° C. for 2 hours. After the digestion with HindIII, the larger plasmid DNA fragment of about 4.33 Kb was purified by LGT method.

About 50 ng of the DNA fragment of about 100 bp containing the trp promoter and obtained above, about 0.2 µg of the DNA fragment of about 4.33 Kb derived from pBR322 and obtained above, and 50 ng of 5'-phosphorylated XhoI linker (pCCTCGAGG, product of Collaborative Research) were ligated with 1 unit of T4 DNA ligase in 20 µl (total volume) of a reaction solution consisting of 20 mM Tris-HCl (pH 7.6), 10 mM MgCl$_2$, 10 mM dithiothrettol and 0.5 mM ATP at 4° C. for 40 hours. Escherichia coli HB101 was transformed with the thus obtained recombinant plasmid DNA and plasmid DNAs were isolated and purified from the ApRTc$^R$ transformants. These plasmid DNAs were digested with restriction enzymes, EcoRI, XhoI, HindIII, HaeIII, ClaI, TaqI (product of Bethesda Research Laboratories Inc.) and RsaI (product of New England Biolabs) to select the plasmid wherein the DNA fragment of about 100 bp containing the trp promoter and XhoI linker were cloned. This plasmid was named pKYP100.

REFERENCE EXAMPLE 3

Construction of plasmid vector pTrS3 bearing the initiation codon for translation ATG and SphI cleavage site downstream from the trp promoter and the ribosome binding site:

Plasmid pTrS3 was obtained from pKYP100 constructed as in Reference Example 2 in the following manner. 5 µg of pKYP100 was allowed to react with 5 units of ClaI in 20 µl (total volume) of a reaction solution consisting of 10 mM Tris-HCl (pH 7.5), 7 mM MgCl$_2$ and 6 mM 2-mercaptoethanol at 37° C. for 2 hours. The reaction was stopped by heating at 65° C. for 5 minutes. Then, 2 µl of 100 mM Tris-HCl (pH 7.5), 70 mM MgCl$_2$, 1.0M NaCl, 60 mM 2-mercaptoethanol, 16 µl of distilled water and 7 units of SphI (product of Boehringer Mannheim GmbH) were added and the mixture was allowed to react at 37° C. for 2 hours. The reaction was stopped by heating at 65° C. for 5 minutes and the larger plasmid DNA fragment (about 3.82 Kb) was purified by LGT method.

Separately, two species of oligonucleotides, 5'-CGATAAGCTATGCATG-3' and 5'-CATAGCTTAT-3' were synthesized by the phosphotriester method. The two synthesized oligonucleotides were 5'-phosphorylated and 20 µM each the oligonucleotides were mixed with 10 mM Tris-HCl (pH 7.5), 100 mM NaCl and 1 mM EDTA. The mixture was incubated at 65° C. for 10 minutes, at 37° C. for 120 minutes and at room temperature for 120 minutes to anneal them. The two DNA chains were annealed as illustrated below.

pCGATAAGCTATGCATG
TATTCGATACp

Both ends of the resulting DNA fragment can be ligated with the DNA fragment having sticky ends formed by digestion with ClaI or SphI and hhe ligated DNA has a ClaI cleavage site or SphI cleavage site for reconstruction. The annealed DNA of the two oligonucleotides and the plasmid DNA fragment purified as above were mixed and ligated with T4 DNA ligase. That is, 1 pmole each of the two oligonucleotides, pCGATAAGCTATGCATG and pCATAGCTTAT were annealed and about 0.15 µg of the purified plasmid DNA fragment was added. Then, 0.5 unit of T4 DNA ligase was added and the mixture was allowed to react in 20 µl (total volume) of a reaction solution consisting of 20 mM Tris-HCl (pH 7.6), 10 mM MgCl$_2$, 10 mM dithiothreitol and 0.5 mM ATP at 4° C. for 16 hours.

Escherichia coli HB101 was transformed with the resulting recombinant plasmid DNA. Plasmid DNAs were isolated from the thus obtained transformant resistant to ampicillin and sensitive to tetracycline (ApRTcS) and purified. These plasmid DNAs were digested with EcoRI, XhoI, PstI, ClaI and SphI to recognize the formation of the desired plasmid vector pTrS3. It was recognized by the method of Maxam and Gilbert [A. M. Maxam, et al.: Proc. Natl. Acad. Sci., 74, 560 (1977)] that the base sequence of the DNA between the ClaI site and SphI site of pTrS3 was ATCGATAAGCTATGCATGC. Escherichia coli containing pTrS3 has been deposited with the Fermentation Research Institute, Agency of Industrial Science and Technology as Escherichia coli ITrS-3, FERM BP-328.

What is claimed is:

1. A fused protean of an adult T cell leukemia virus antigen peptide and β-galactosidase, said antigen peptide consisting of 198 amino acids starting from the 17th amino acid (Met) of the N-terminal of p24 and 23 amino acids which are the product of gag gene other than p24 at the C-terminal and said β-galactosidase lacking 7 amino acids from the N-terminal, wherein said fused protein or part thereof evidences immune agglutination with anti-ATLA antibody.

* * * * *

UNITED STATES PATENT AND TRADEMARK OFFICE
CERTIFICATE OF CORRECTION

PATENT NO. : 4,795,805

DATED : January 3, 1989

INVENTOR(S) : SEIGA ITOH, ET AL.

It is certified that error appears in the above-identified patent and that said Letters Patent is hereby corrected as shown below:

Cover Page, at [56] "Other Publications", "Casadahm" should read: --Casadaban--; "Oroszlon" should read: --Oroszlan--; "Hinumn" should read: --Hinuma--; "Hamura" should read: --Itamura--; "Gay" should read: --Gag--; "Germaini" should read: --Germino--; "R6IL" should read: --R6K--; "Weinstach" should read: --Weinstock--.

Column 6, line 47, "HinII" should read:
  --HinfI--.

Column 7, line 5, "1" should read: --10--;
       line 26, "(pH 7.1)" should read:
  --(pH 7.5)--;
       line 42, "RAS 23 and" should read:
  --and has 23--;
       line 62, "337°" should read: --37°--.

UNITED STATES PATENT AND TRADEMARK OFFICE
CERTIFICATE OF CORRECTION

PATENT NO. : 4,795,805

DATED : January 3, 1989

INVENTOR(S) : SEIGA ITOH, ET AL.

It is certified that error appears in the above-identified patent and that said Letters Patent is hereby corrected as shown below:

Column 8, line 32, "0.5% camamino" should read:
   --0.5% glucose, 0.5% casamino--.

Column 11, line 29, "dithiothrettol" should read:
   --dithiothreitol--.

Column 12, line 48, "protean" should read:
   --protein--.

Signed and Sealed this

Twenty-seventh Day of June, 1989

Attest:

DONALD J. QUIGG

Attesting Officer

Commissioner of Patents and Trademarks